United States Patent
Iaccino et al.

(10) Patent No.: US 10,611,705 B2
(45) Date of Patent: Apr. 7, 2020

(54) PROCESS FOR CONVERSION OF ACYCLIC $C_5$ COMPOUNDS TO CYCLIC $C_5$ COMPOUNDS AND FORMULATED CATALYST COMPOSITIONS USED THEREIN

(71) Applicant: ExxonMobil Chemical Patents Inc., Baytown, TX (US)

(72) Inventors: Larry L. Iaccino, Seabrook, TX (US); Xiaoying Bao, Houston, TX (US); Chuansheng Bai, Phillipsburg, NJ (US); Jeremy W. Bedard, Humble, TX (US); Jocelyn A. Gilcrest, Mullica Hill, NJ (US); Wenyih F. Lai, Bridgewater, NJ (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 6 days.

(21) Appl. No.: 15/949,104

(22) Filed: Apr. 10, 2018

(65) Prior Publication Data
US 2018/0319722 A1    Nov. 8, 2018

Related U.S. Application Data

(60) Provisional application No. 62/500,814, filed on May 3, 2017.

(51) Int. Cl.
*C07C 5/333* (2006.01)
*B01J 29/44* (2006.01)
(Continued)

(52) U.S. Cl.
CPC .............. *C07C 5/3337* (2013.01); *B01J 29/44* (2013.01); *B01J 29/46* (2013.01); *B01J 35/026* (2013.01);
(Continued)

(58) Field of Classification Search
None
See application file for complete search history.

(56) References Cited

U.S. PATENT DOCUMENTS

| | | | | |
|---|---|---|---|---|
| 4,458,025 A | * | 7/1984 | Lee ........................ | B01J 29/064 502/66 |
| 4,634,518 A | * | 1/1987 | Buss ...................... | B01J 29/605 208/138 |

(Continued)

OTHER PUBLICATIONS

Haber et al. Manual of Methods and Procedures for Catalyst Characterization (Technical report). 1996. Pure & Applied Chemistry vol. 67, Nos. 8/9 pp. 1257-1306 (Year: 1996).*

(Continued)

*Primary Examiner* — In Suk C Bullock
*Assistant Examiner* — Alyssa L Cepluch
(74) *Attorney, Agent, or Firm* — Kevin M. Faulkner

(57) ABSTRACT

Disclosed is a process for the conversion of acyclic $C_5$ feedstock to a product comprising cyclic $C_5$ compounds, including cyclopentadiene, and formulated catalyst compositions for use in such process. The process comprises contacting the feedstock and, optionally, hydrogen under acyclic $C_5$ conversion conditions in the presence of a catalyst composition to form the product. The catalyst composition comprises a microporous crystalline metallosilicate, a Group 10 metal or compound thereof, a binder, optionally, a metal selected from the group consisting of rare earth metals, metals of Groups 8, 9, or 11, mixtures or combinations thereof, or a compound thereof, in combination with a Group 1 alkali metal or a compound thereof and/or a Group 2 alkaline earth metal or a compound thereof.

17 Claims, 4 Drawing Sheets

(51) Int. Cl.
*B01J 37/02* (2006.01)
*C07C 5/387* (2006.01)
*B01J 29/46* (2006.01)
*B01J 35/02* (2006.01)
*B01J 35/08* (2006.01)
*C07C 5/373* (2006.01)
*B01J 37/04* (2006.01)
*B01J 37/08* (2006.01)
*B01J 35/10* (2006.01)
*B01J 21/08* (2006.01)
*B01J 21/16* (2006.01)

(52) U.S. Cl.
CPC ............ *B01J 35/08* (2013.01); *B01J 35/1066* (2013.01); *B01J 37/0201* (2013.01); *B01J 37/04* (2013.01); *B01J 37/088* (2013.01); *C07C 5/373* (2013.01); *C07C 5/387* (2013.01); *B01J 21/08* (2013.01); *B01J 21/16* (2013.01); *B01J 2229/42* (2013.01); *C07C 2521/04* (2013.01); *C07C 2521/08* (2013.01); *C07C 2521/16* (2013.01); *C07C 2529/44* (2013.01); *C07C 2529/46* (2013.01); *C07C 2601/08* (2017.05); *C07C 2601/10* (2017.05)

(56) References Cited

U.S. PATENT DOCUMENTS

| | | | |
|---|---|---|---|
| 4,673,664 A * | 6/1987 | Bambrick | C10G 45/04 502/439 |
| 4,861,932 A * | 8/1989 | Chen | C07C 5/417 585/412 |
| 4,990,710 A * | 2/1991 | Dessau | B01J 29/44 208/143 |
| 5,284,986 A * | 2/1994 | Dessau | B01J 29/44 585/311 |
| 6,429,339 B1 | 8/2002 | Liang et al. | |
| 6,936,561 B2 * | 8/2005 | Marques | B01D 53/885 502/60 |
| 9,856,187 B2 | 1/2018 | Iaccino et al. | |
| 2009/0036692 A1 | 2/2009 | Shimizu et al. | |
| 2009/0301934 A1* | 12/2009 | Miller | C10G 35/09 208/65 |
| 2010/0234657 A1* | 9/2010 | Takamatsu | B01J 29/061 585/419 |
| 2013/0211082 A1 | 8/2013 | Kerschen | |
| 2016/0046553 A1 | 2/2016 | Matsuura et al. | |
| 2017/0121245 A1 | 5/2017 | Iaccino et al. | |
| 2017/0121246 A1 | 5/2017 | Iaccino et al. | |
| 2017/0121247 A1 | 5/2017 | Iaccino et al. | |
| 2017/0121253 A1 | 5/2017 | Iaccino et al. | |

OTHER PUBLICATIONS

DieselNet "Catalytic Coating & Materials" DieselNet.com. 2005 (Year: 2005).*

Fel'dblyurn, V.S., et al. "Cyclization and dehydrocyclization of C5 hydrocarbons over platinum nanocatalysts and in the presence of hydrogen sulfide," Doklady Chemistry, vol. 424, pp. 27-30, 2009.

* cited by examiner

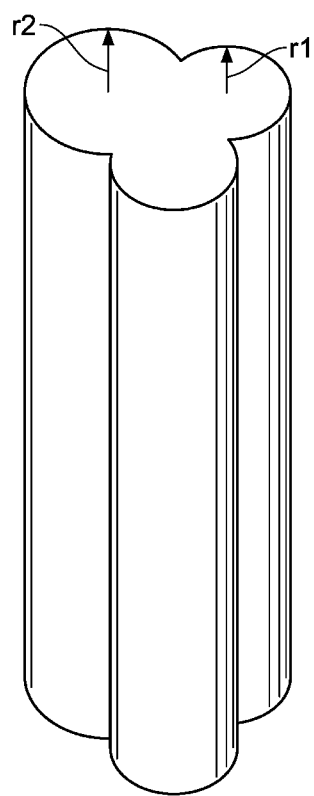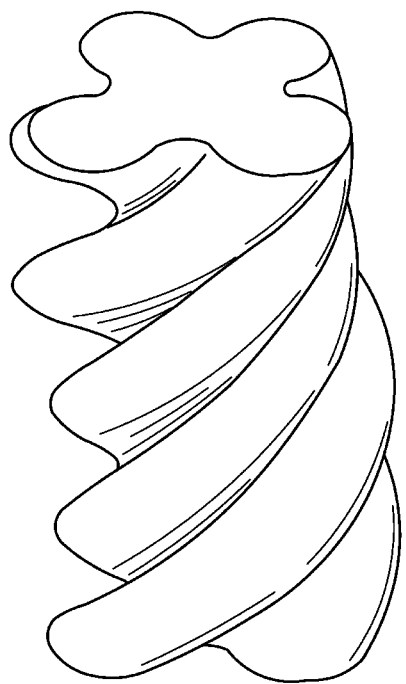
FIG. 3A
FIG. 3B

PROCESS FOR CONVERSION OF ACYCLIC C$_5$ COMPOUNDS TO CYCLIC C$_5$ COMPOUNDS AND FORMULATED CATALYST COMPOSITIONS USED THEREIN

CROSS-REFERENCE TO RELATED APPLICATION

This application claims priority to U.S. Provisional Application No. 62/500,814, filed May 3, 2017, the disclosure of which is incorporated herein by reference.

FIELD OF THE INVENTION

This invention relates to a formulated catalyst compositions and their use in a process for the conversion of an acyclic C$_5$ feedstock to a product comprising cyclic C$_5$ compounds, such as for example, cyclopentadiene.

BACKGROUND OF THE INVENTION

Cyclopentadiene (CPD) and its dimer dicyclopentadiene (DCPD) are highly desired raw materials used throughout the chemical industry in a wide range of products such as polymeric materials, polyester resins, synthetic rubbers, solvents, fuels, fuel additives, etc. In addition, cyclopentane and cyclopentene are useful as solvents, and cyclopentene may be used as a monomer to produce polymers and as a starting material for other high value chemicals.

Cyclopentadiene (CPD) is currently a minor byproduct of liquid fed steam cracking (for example, naphtha and heavier feed). As existing and new steam cracking facilities shift to lighter feeds, less CPD is produced while demand for CPD is rising. High cost due to supply limitations impacts the potential end product use of CPD in polymers. More CPD-based polymer products and other high value products could be produced, if additional CPD could be produced, at unconstrained rates and preferably at a cost lower than recovery from steam cracking.

It was previously discovered that CPD may be produced as the primary product from plentiful C$_5$ feedstock using a catalyst system in a process to produce CPD while minimizing production of light (C$_{4-}$) byproducts. In view of this discovery, there remains a need for optimization of catalyst formulation used in the catalyst system. This invention meets this and other needs.

Related publications include US 2017/121253; and US 2017/121247.

SUMMARY OF THE INVENTION

In one aspect, the invention relates to a process for producing cyclic C$_5$ compounds including cyclopentadiene. The process comprises (or consisting of, or consisting essentially of) the step of contacting a feedstock with a formulated catalyst composition under acyclic C$_5$ conversion conditions effective to convert at least part of the acyclic C$_5$ feedstock to produce an effluent comprising one or more cyclic C$_5$ compounds. The acyclic C$_5$ feedstock comprises acyclic C$_5$ hydrocarbons and optionally hydrogen, a light hydrocarbon or a mixture thereof. The formulated catalyst composition comprises:

(i) a microporous crystalline metallosilicate, preferably, having a constraint index less than or equal to 12;
(ii) a metal of Group 10 of the Periodic Table or a compound thereof, and optionally, a metal selected from the group consisting of rare earth metals, metals of Groups 8, 9, or 11 of the Periodic Table, mixtures or combinations thereof, or a compound thereof;
(iii) a binder comprising (or consisting of, or consisting essentially of) one or more of silica, titania, zirconia, metal silicates of Group 1, Group 2, or Group 13 of the Periodic Table and mixtures thereof;
(iv) an alkali metal of Group 1 of the Periodic Table, or a compound thereof; and/or
(v) an alkaline earth metal of Group 2 of the Periodic Table or a compound thereof.

Advantageously, the formulated catalyst composition may be made into one or more of an extrudate, a spray dried particle, an oil drop particle, a mulled particle, or a spherical particle. In In any embodiment, the extrudate is a shaped extrudate which may be in cylindrical form or a lobed form. The shaped extrudate in lobed form may be a symmetrical lobed form, an asymmetrical lobed form, a symmetrical spiral lobed form or an asymmetrical spiral lobed form.

Advantageously, the binder comprises one or more of silica, titania, zirconia, metal silicates, calcium silicate, magnesium silicate, and mixtures thereof.

Advantageously, at least a portion of the formulated catalyst composition may be deposited on a microlith support or a monolith support.

Conveniently, the microporous crystalline metallosilicate has a framework type selected from the group consisting of MWW, MFI, LTL, MOR, BEA, TON, MTW, MTT, FER, MRE, MFS, MEL, DDR, EUO, and FAU. In In any embodiment, the microporous crystalline metallosilicate is a microporous crystalline aluminosilicate.

Conveniently, the alkali metal is preferably sodium; the alkaline earth metal is preferably magnesium.

Conveniently, the metal of Group 10 is preferably platinum, and the optional metal is a Group 11 metal, preferably copper or silver.

In other aspects, the invention relates to a cyclic C$_5$ composition which comprises one or more of the cyclic C$_5$ compounds which are made by the process of this invention. The cyclic C$_5$ composition may be reacted with a substrate comprising a double bond to form a product. Such product may be included in an article.

BRIEF DESCRIPTION OF THE FIGURES

FIG. 3A is a graphical representation of a shaped extrudate in asymmetrical lobed form.

FIG. 3B is a graphical representation of a shaped extrudate in asymmetrical spiral lobed form.

DETAILED DESCRIPTION OF THE INVENTION

The inventors have found that processes useful converting acyclic C$_5$ feedstocks to cyclic C$_5$ compounds are preferably carried out in fluided bed or moving bed-type reactors, and thus, the quality of the molecular sieve or zeolite-type catalyst to maintain its physical integrity is improved by using less clay and/or alumina as a binder, preferably replacing these materials with silica-type materials.

Definitions

For the purpose of this specification and appended claims, the following terms are defined.

The term "hydrocarbon" means a class of compounds containing hydrogen bound to carbon, and encompasses (i) saturated hydrocarbon compounds, (ii) unsaturated hydrocarbon compounds, and (iii) mixtures of hydrocarbon compounds (saturated and/or unsaturated), including mixtures of hydrocarbon compounds. The term "$C_n$" means hydrocarbon(s) having n carbon atom(s) per molecule, wherein n is a positive integer.

The term "$C_5$ feedstock" includes a feedstock containing n-pentane, such as, for example, a feedstock which is predominately normal pentane and isopentane (also referred to as methylbutane), with smaller fractions of cyclopentane and neopentane (also referred to as 2,2-dimethylpropane).

As used herein, the term "light hydrocarbon" means light paraffinic and/or olefinic hydrocarbons comprised substantially of hydrogen and carbon only and has one to no more than 4 carbon atoms.

As used herein, the term "Periodic Table" means the IUPAC Periodic Table of the Elements, dated 1 May 2013, as it appears on the inside cover of The Merck Index, Twelfth Edition, Merck & Co., Inc., 1996.

Figure 1:
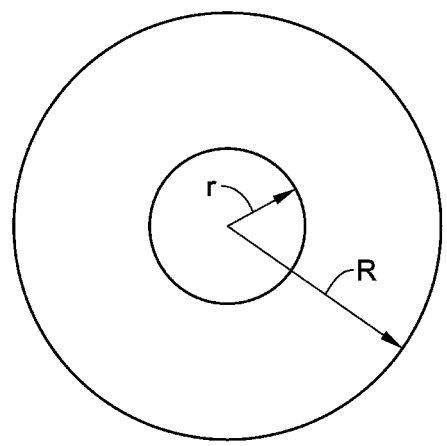
FIG. 1 is a graphical representation of a cross-section of a shaped extrudate in cylindrical form.

As used herein, the term "cylindrical" when referring to a shaped extrudate means an extrudate having the shape substantially as shown in FIG. 1, wherein the inner radius, r, is less than the outer radius, R; including r=0.

As used herein, the term "spherical particle" means a particle that is substantially in the shape of a sphere which is a round solid having a surface in which every point is equidistant from the center of the sphere. For the purpose of this invention particles for which distance from surface to surface points differ by +/−25% will also be considered spherical.

Figures 2A, 2B:
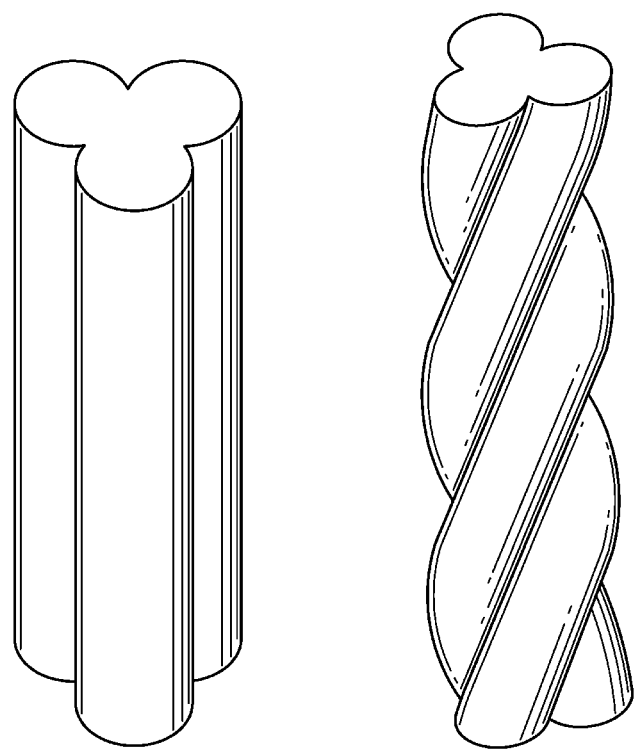
FIG. 2A is a graphical representation of a shaped extrudate in symmetrical lobed form.
FIG. 2B is a graphical representation of a shaped extrudate in symmetrical spiral lobed form.

As used herein, the term "symmetrical lobed form" when referring to a shaped extrudate means an extrudate having the shape substantially as shown in FIG. 2A.

As used herein, the term "symmetrical spiral lobed form" when referring to a shaped extrudate means an extrudate having the shape substantially as shown in FIG. 2B.

As used herein, the term "asymmetrical lobed form" when referring to a shaped extrudate means an extrudate having the shape substantially as shown in FIG. 3A, wherein the radius, $r_2$ is greater than the radius, $r_1$.

As used herein, the term "asymmetrical spiral lobed form" when referring to a shaped extrudate means an extrudate having the shape substantially as shown in FIG. 3B.

As used herein, the term "washcoat" means a catalyst composition which is formulated into a slurry that is deposited on a catalyst support and then dried.

As used herein, the term "monolith" when referring to a catalyst support means a monolithic catalyst support which is placed in an orderly pattern in a reactor and which comprises a plurality channels separated by walls that are coated with a catalytic composition.

As used herein, the term "microlith" when referring to a catalyst support means a catalyst support that is randomly loaded into a reactor and which comprises a one or more channels and/or surfaces that are coated with a catalytic composition.

The term "saturate" or "saturated" includes, but is not limited to, alkanes and cycloalkanes.

The term "non-saturates" includes, but is not limited to, alkenes, dialkenes, alkynes, cyclo-alkenes and cyclo-dialkenes.

The term "cyclic $C_5$" or "$cC_5$" includes, but is not limited to, cyclopentane, cyclopentene, cyclopentadiene, and mixtures of two or more thereof. The term "cyclic $C_5$" or "$cC_5$" also includes alkylated analogs of any of the foregoing, e.g., methyl cyclopentane, methyl cyclopentene, and methyl cyclopentadiene. It should be recognized for purposes of the invention that cyclopentadiene spontaneously dimerizes over time to form dicyclopentadiene via Diels-Alder condensation over a range of conditions, including ambient temperature and pressure.

The term "acyclic" includes, but is not limited to, linear and branched saturates and non-saturates.

The term "aromatic" means a planar cyclic hydrocarbyl with conjugated double bonds, such as, for example, benzene. As used herein, the term aromatic encompasses compounds containing one or more aromatic rings, including, but not limited to, benzene, toluene, and xylene, and polynuclear aromatics (PNAs), which include, but are not limited to, naphthalene, anthracene, chrysene, and their alkylated versions. The term "$C_{6+}$ aromatics" includes compounds based upon an aromatic ring having six or more ring atoms, including, but not limited to, benzene, toluene, and xylene and polynuclear aromatics (PNAs) which include, but are not limited to, naphthalene, anthracene, chrysene, and their alkylated versions.

The term "Group 10 metal" means an element in Group 10 of the Periodic Table and includes, but is not limited to, nickel, palladium, platinum, and a mixture of two or more thereof.

The term "Group 11 metal" means an element in Group 11 of the Periodic Table and includes, but is not limited to, copper, silver, gold, and a mixture of two or more thereof.

The term "Group 1 alkali metal" means an element in Group 1 of the Periodic Table and includes, but is not limited to, lithium, sodium, potassium, rubidium, cesium, and a mixture of two or more thereof, and excludes hydrogen.

The term "Group 2 alkaline earth metal" means an element in Group 2 of the Periodic Table and includes, but is not limited to, beryllium, magnesium, calcium, strontium, barium, and a mixture of two or more thereof.

The term "rare earth metal" means an element in the Lanthanide series of the Periodic Table, as well as scandium and yttrium. The term rare earth metal includes, but is not limited to, lanthanum, praseodymium, neodymium, cerium, yttrium, and a mixture of two or more thereof.

The term "constraint index" is defined in U.S. Pat. Nos. 3,972,832 and 4,016,218, both of which are incorporated herein by reference.

As used herein, the term "MCM-22 family material" includes one or more of:

(i) molecular sieves made from a common first degree crystalline building block unit cell, which unit cell has the MWW framework topology (A unit cell is a spatial arrangement of atoms which if tiled in three-dimensional space describes the crystal structure. Such crystal structures are discussed in the "Atlas of Zeolite Framework Types," Fifth edition, 2001, the entire content of which is incorporated as reference.);

(ii) molecular sieves made from a common second degree building block, being a 2-dimensional tiling of such MWW framework topology unit cells, forming a monolayer of one unit cell thickness, preferably one c-unit cell thickness;

(iii) molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks may be in a regular fashion, an irregular fashion, a random fashion, or any combination thereof; and (iv) molecular sieves made by any regular or random 2-dimensional or 3-dimensional combination of unit cells having the MWW framework topology.

The MCM-22 family material includes those molecular sieves having an X-ray diffraction pattern including d-spacing maxima at 12.4±0.25, 6.9±0.15, 3.57±0.07, and 3.42±0.07 Angstrom. The X-ray diffraction data used to characterize the material are obtained by standard techniques using the K-alpha doublet of copper as incident radiation and a diffractometer equipped with a scintillation counter and associated computer as the collection system.

As used herein, the term "molecular sieve" is used synonymously with the term "zeolite" or "microporous crystalline material."

As used herein, the term "selectivity" means the moles of carbon in the respective cyclic $C_5$, CPD, $C_1$, and $C_{2-4}$ formed divided by total moles of carbon in the pentane converted. For example, the term "carbon selectivity to cyclic $C_5$ of at least 30%" means that at least 30 moles of carbon in the cyclic $C_5$ is formed per 100 moles of carbon in the pentane converted.

As used herein, the term "conversion" means the moles of carbon in the acyclic $C_5$ feedstock that is converted to a product. The term "conversion of at least 70% of the acyclic $C_5$ feedstock to a product" means that at least 70% of the moles of the acyclic $C_5$ feedstock was converted to a product.

The term "coke" includes, but is not limited to, a low hydrogen content hydrocarbon that is adsorbed on the catalyst composition.

As used herein, the term "Alpha Value" is used as a measure of the cracking to activity of a catalyst and is described in U.S. Pat. No. 3,354,078 and in the Journal of Catalysis, Vol. 4, p. 527 (1965); Vol. 6, p. 278, (1966) and Vol. 61, p. 395, (1980), each incorporated herein by reference.

As used herein, the term "reactor" refers to any vessel(s) in which a chemical reaction occurs. Reactor includes both distinct reactors, as well as reaction zones within a single reactor apparatus and, as applicable, reactions zones across multiple reactors. For example, a single reactor may have multiple reaction zones. Where the description refers to a first and second reactor, the person of ordinary skill in the art will readily recognize such reference includes two reactors, as well as a single reactor vessel having first and second reaction zones. Likewise, a first reactor effluent and a second reactor effluent will be recognized to include the effluent from the first reaction zone and the second reaction zone of a single reactor, respectively.

As used herein, the term "adiabatic reactor" includes a reactor/reaction zone may be an adiabatic reactor/reaction zone or a diabatic reactor/reaction zone. As used herein, the term "adiabatic" refers to a reaction zone for which there is essentially no heat input into the system other than by a flowing process fluid. A reaction zone that has unavoidable losses due to conduction and/or radiation may also be considered adiabatic for the purpose of this invention.

As used herein, the term "diabatic" refers to a reactor/reaction zone to which heat is supplied by a means in addition to that provided by the flowing process fluid.

As used herein, the term "fluidized bed" reactor refers to a zone or vessel with contacting of solids (e.g., catalyst particles) and gas flows such that the superficial gas velocity (U) is sufficient to fluidize solid particles (i.e., above the minimum fluidization velocity Umf) and is below the velocity required for dilute-phase pneumatic conveying of solid particles in order to maintain a solids bed with void fraction below 95%. A fluidized bed reactor may be a moving fluidized bed reactor, such as a "circulating fluidized bed reactor," which refers to a fluidized bed with a movement of solids (e.g., catalyst material) through the reactor and at least a partial recirculation of the solids (e.g., catalyst material). For example, the solids (e.g., catalyst material) may have been removed from the reactor, regenerated, reheated, and/or separated from the product stream and then returned back to the reactor. A fluidized bed reactor includes a reactor with cascaded fluid beds, as defined below.

As used herein, the term "cascaded fluid-beds" means a series arrangement of individual fluid-beds such that there can be a gradient in gas and/or solid property (such as, temperature, gas, or solid composition, pressure, etc.) as the solid or gas cascades from one fluid-bed to another. Locus of minimum fluidization velocity is given in, for example, Kunii, D., Levenspiel, O., Chapter 3 of Fluidization Engineering, 2nd Edition, Butterworth-Heinemann, Boston, 1991 and Walas, S. M., Chapter 6 of Chemical Process Equipment, Revised 2nd Edition, Butterworth-Heinemann, Boston, 2010.

As used herein, the term "moving bed" reactor refers to a zone or vessel with contacting of solids (e.g., catalyst particles) and gas flows such that the superficial gas velocity (U) is below the velocity required for dilute-phase pneumatic conveying of solid particles in order to maintain a solids bed with void fraction below 95%. In a moving bed reactor, the solids (e.g., catalyst material) may slowly travel through the reactor and may be removed from the bottom of the reactor and added to the top of the reactor. A moving bed reactor may operate under several flow regimes, including settling or moving packed-bed regime (U<Umf), bubbling regime (Umf<U<Umb), slugging regime (Umb<U<Uc), transition to and turbulent fluidization regime (Uc<U<Utr), and fast-fluidization regime (U>Utr), where Umf is minimum fluidizing velocity, Umb is minimum bubbling velocity, Uc is the velocity at which fluctuation in pressure peaks, and tr is transport velocity. These different fluidization regimes have been described in, for example, Kunii, D., Levenspiel, O., Chapter 3 of Fluidization Engineering, 2nd Edition, Butterworth-Heinemann, Boston, 1991 and Walas, S. M., Chapter 6 of Chemical Process Equipment, Revised 2nd Edition, Butterworth-Heinemann, Boston, 2010, which are incorporated by reference.

As used herein, the term "fixed bed" or "packed bed" reactor refers to a zone or vessel (such as, vertical or horizontal, cylindrical pipe or a spherical vessel) and may include transverse (also known as cross flow), axial flow, and/or radial flow of the gas, where solids (e.g., catalyst particles) are substantially immobilized within the reactor and gas flows such that the superficial velocity (U) is below the velocity required to fluidize the solid particles (i.e., below the minimum fluidization velocity Umf) and/or the gas is moving in a downward direction so that solid particle fluidization is not possible.

As used herein, the term "tubular reactor" means a reactor having reactor tubes that are straight rather than having a coiled or curved path through the enclosure (although coiled or curved tubes may be used). Additionally, the tubes may have a cross section that is circular, elliptical, rectangular, and/or other known shapes. The tubes are preferentially heated with a turbine exhaust stream produced by a turbine burning fuel gas with a compressed gas comprising oxygen. In other aspects, the reactor tubes are heated by convection with hot gas produced by combustion in a furnace, boiler, or excess air burner. However, heating the reactor tubes with turbine exhaust is preferred because of the co-production of shaft power among other advantages.

As used herein, the term "radiantly heated tubular" reactor refers to a furnace and parallel reactor tube(s) positioned within a radiant section of the furnace. The reactor tubes contain a catalytic material (e.g., catalyst particles), which contacts reactant(s) to form a product.

As used herein, the term "convectively heated tubular" reactor refers to a conversion system comprising parallel reactor tube(s) containing a catalytic material and positioned within an enclosure. While any known reactor tube configuration or enclosure may be used, preferably the conversion system comprises multiple parallel reactor tubes within a convective heat transfer enclosure.

As used herein, the term "cyclical" or "cyclically" refers to a periodic recurring or repeating event that occurs according to a cycle. For example, reactors (e.g., cyclic fixed bed) may be cyclically operated to have a reaction interval, a reheat interval, and/or a regeneration interval. The duration and/or order of the interval steps may change over time.

Acyclic $C_5$ Conversion Process

One aspect of the invention relates to a process for producing cyclic $C_5$ compounds including cyclopentadiene. The process comprises the step of contacting an acyclic $C_5$ feedstock, defined herein, with a formulated catalyst composition, discussed herein, under acyclic $C_5$ conversion conditions effective to convert at least part of the acyclic $C_5$ feedstock to produce an effluent comprising one or more cyclic $C_5$ compounds. The acyclic $C_5$ feedstock comprises acyclic $C_5$ hydrocarbons and optionally hydrogen, a light hydrocarbon or a mixture thereof.

The acyclic $C_5$ conversion conditions for the process of this invention include at least a temperature of 450° C. to 650° C. The molar ratio of the optional hydrogen co-feed to the acyclic $C_5$ feedstock is in the range of 0.01 to 3. The molar ratio of the optional light hydrocarbon co-feed to the acyclic $C_5$ feedstock is in the range of 0.01 to 5. The acyclic $C_5$ feedstock can have a partial pressure in the range of 3 psia to 100 psia at the reactor inlet (21 to 689 kPa-a). The acyclic $C_5$ feedstock can have a weight hourly space velocity in the range from 1 $hr^{-1}$ to 50 $hr^{-1}$.

As used herein, "consisting essentially of" with respect to compositions means that the composition includes no more than 5, or 4, or 3, or 2, or 1 wt %, by weight of the composition, of any components that will alter the purpose and function of such composition, such as, for instance, a binder having less than 5 wt % alumina and/or clay, or some other additive necessary or desirable to carry out the claimed invention and maintain or improves the desired yield of hydrocarbon product; and with respect to a process, means that no other steps or process features are present that will alter the fundamental nature of the claimed steps and process features, but can include additional process steps and features that a person of skill in the art would understand are necessary or desirable to carry out the claimed invention and maintain or improves the desired yield of hydrocarbon product.

Feedstock

The acyclic $C_5$ feedstock useful in the invention herein is obtainable from crude oil or natural gas condensate, and can include cracked $C_5$ (in various degrees of unsaturation: alkenes, dialkenes, alkynes) produced by refining and chemical processes, such as fluid catalytic cracking (FCC), reforming, hydrocracking, hydrotreating, coking, and steam cracking.

The acyclic $C_5$ feedstock useful in the process of this invention comprises pentane, pentene, pentadiene, and mixtures of two or more thereof. Preferably, the acyclic $C_5$ feedstock comprises at least about 50 wt %, or 60 wt %, or 75 wt %, or 90 wt % n-pentane, or in the range from about 50 wt % to about 100 wt % n-pentane, by weight of the feedstock.

The acyclic $C_5$ feedstock, optionally, does not comprise $C_6$ aromatic compounds, such as, benzene, preferably $C_6$ aromatic compounds are present at less than 5 wt %, preferably less than 1 wt %, preferably present at less than 0.01 wt %, preferably at 0 wt %, by weight of the feedstock.

The acyclic $C_5$ feedstock, optionally, does not comprise benzene, toluene, or xylene (ortho, meta, or para). Preferably, any benzene, toluene, or xylene (ortho, meta, or para) compounds are present at less than 5 wt %, preferably less than 1 wt %, preferably present at less than 0.01 wt %, preferably at 0 wt %, by weight of the feedstock.

The acyclic $C_5$ feedstock, optionally, does not comprise $C_{6+}$ aromatic compounds, preferably $C_{6+}$ aromatic compounds are present at less than 5 wt %, preferably less than 1 wt %, preferably present at less than 0.01 wt %, preferably at 0 wt %, by weight of the feedstock.

The acyclic $C_5$ feedstock optionally does not comprise $C_{4-}$ compounds, any $C_{4-}$ compounds are present at less than 5 wt %, preferably less than 1 wt %, preferably present at less than 0.01 wt %, preferably at 0 wt %, by weight of the feedstock.

Catalyst Composition

The formulated catalyst composition comprises a microporous crystalline metallosilicate, preferably, having a constraint index of less than or equal to 12 and a binder, and includes a Group 10 metal of the Periodic Chart or a compound thereof, and, optionally, a metal selected from the rare earth metals and Groups 8, 9, and 11 of the Periodic Chart, mixture or combinations thereof, or a compound thereof, in combination with a Group 1 alkali metal and/or a Group 2 alkaline earth metal or a compound thereof.

Preferred optional metals are Group 11 metals. Typically, the Group 11 metal is selected from the group consisting of Cu, Ag, Au, and mixtures of two or more thereof; preferably Cu or Ag. A preferred optional Group 9 metal is Rh, which may form an alloy with the Group 10 metal. Typically, the optional rare earth metal is selected from the group consisting of yttrium, lanthanum, cerium, praseodymium, and mixtures or combinations thereof.

The alkali metal includes or is selected from the group consisting of lithium, sodium, potassium, rubidium, cesium, and mixtures of two or more thereof.

The alkaline earth metal is selected from the group consisting of beryllium, magnesium, calcium, strontium, barium, and mixtures of two or more thereof.

The microporous crystalline metallosilicate has a framework type selected from the group consisting of MWW, MFI, LTL, MOR, BEA, TON, MTW, MTT, FER, MRE, MFS, MEL, DDR, EUO, and FAU. In In any embodiment, the microporous crystalline metallosilicate is preferably a microporous crystalline aluminosilicate or zeolite. The microporous crystalline aluminosilicate is selected from the group consisting of zeolite beta, mordenite, faujasite, Zeolite L, ZSM-5, ZSM-11, ZSM-22, ZSM-23, ZSM-35, ZSM-48, ZSM-50, ZSM-57, ZSM-58, MCM-22 family material, and mixtures of two or more thereof.

In or more embodiments, the metallosilicate comprises aluminum and the molar ratio of the alkali metal to aluminum is at least 1. In other embodiments, the molar ratio of the alkaline earth metal to aluminum is at least 1.

The catalyst composition is made by the method according to the Examples, below.

The source of platinum, a Group 10 metal, included and may be selected from the group consisting of platinum nitrate, chloroplatinic acid, platinous chloride, platinum amine compounds, tetraamine platinum hydroxide, and mixtures of two or more thereof. The source of copper, a Group 11 metal, includes and may be selected from the group consisting of copper nitrate, copper nitrite, copper acetate, copper hydroxide, copper acetylacetonate, copper carbonate, copper lactate, copper sulfate, copper phosphate, copper chloride, and mixtures of two or more thereof.

The source of silver, also a Group 11 metal, includes and may be selected from the group consisting of silver nitrate, silver nitrite, silver acetate, silver hydroxide, silver acetylacetonate, silver carbonate, silver lactate, silver sulfate, silver phosphate, and mixtures of two or more thereof.

Formulation of Catalyst Composition

The formulated catalyst composition is typically made into one or more forms. In one form, the formulated catalyst is extruded to form an extrudate, particularly into a shaped extrudate having a geometric form. Such shaped extrudates may be in a cylindrical form or a lobed form. The shaped extrudate having a lobed form may be a symmetrical lobed form, an asymmetric lobed form or a spiral lobed form.

Also, the formulated catalyst composition may be made into a particle, such as, for example, a spray dried particle, an oil drop particle, a mulled particle, or a spherical particle. The formulated catalyst composition may be made into a slurry. Such slurry materials typically contain the microporous crystalline metallosilicate, such as zeolite, and a filler such as a silicate. The binder may be comprised of one or more of silica, titania, zirconia, metal silicates of Group 1, Group 2 or Group 13 of the Periodic Table, and mixtures thereof. The use of such slurries are well known in the art of catalysts composition used for wash coating and in catalysts used in fluidized bed processes. Typically such slurries contain aluminum in the form of alumina and or clay; however it was discovery for the catalyst of this invention that a binder containing significant amount of aluminum resulted in poor C5 cyclization activity and undersirable cracking to C4- and skeletal isomerization of acyclic C5 species. Inclusion of alumina in the binder system my be allowable if the alumina is passivated.

In any embodiment, the binder comprises one or more of silica, titania, zirconia, calcium silicate, magnesium silicate, and mixtures thereof.

In any embodiment, the binder contains less than 35 wt % clay and alumina; more preferable less than 10 wt % clay and alumina; most preferably less than 3 wt % clay and alumina, by weight of the binder.

In In any embodiment, the binder is a microporous crystalline metallosilicate which may be the same as or comprises the same material as the microporous crystalline metallosilicate primary crystal or may be a different microporous crystalline metallosilicate. That is, the metal silicate of Group 11 or Group 13 of the Periodic Table comprises a microporous crystalline metallosilicate; preferred are highly siliceous microporous crystalline metallosilicate, i.e., microporous crystalline metallosilicate with a silica to metal molar ration greater than 500. In such case, this material is made by the method of comprising the step of at least partially hydrothermally converting an amorphous metallosilicate by contacting with a source of hydroxy to form the self-bound microporous crystalline metallosilicate.

In In any embodiment, the surface passivated alumina and/or aluminate is produced by treating the alumina with a silica source, a phosphorous source, a boron source, a zinc source, a gallium source, a titanium source, a Group 1 alkali metal or a compound thereof, a Group 2 alkaline earth metal or a compound thereof, and/or a Group 3 rare earth metal or compound thereof (including Yttrium, Lanthanum, Cerium, Praseodymium, and Neodymium); wherein the treating may include thermal or hydrothermal treatment.

Slurry for Washcoating

It is contemplated that the formulated catalyst composition, such as, but not limited to those discussed above, may be made into a slurry. The slurry could be made into the form of a washcoat which is applied to a support. A washcoat, for example, is formed by deagglomerating the sodium form of the zeolite crystals (e.g., Na-ZSM-5), and then the crystals are contacted with sources of the desired Group 10 metal of the Periodic Chart, such as platinum, platinum and silver or platinum and copper, to form a metal-containing Na-ZSM-5. The metal containing Na-ZSM-5 may be heat treated. The metal containing zeolite could be mixed with a binder, a matrix material. The binder could be a mixture of inorganic oxide materials, such as silica, alumina, titania, zirconia and mixtures thereof, to form an aqueous or non-aqueous slurry. The slurry could also contain additives such as defoamers and viscosity modifiers to control the slurry properties. Any surface acidity of alumina in the binder could be either minimized or controlled through the addition of alkaline metals, alkaline earth metals or a source of phosphorus to the slurry. The slurry may be dried, calcined, and deployed in the process for producing cyclic $C_5$ compounds herein.

In any embodiment, the slurry could be applied to the support by means such as spraying or dipping to form a coating on the support. The coated support could be dried. Additional coatings could be applied to form a desired thickness of catalytic material on the support. The final catalytic material receiving the washcoating could be calcined.

Although the slurry can be dried (i.e., pan dried) and calcined directly, it is contemplated that the slurry could be used as a washcoat. In a washcoat, the slurry is deposited on a monolith support or a microlith support or formed into a particle via spray drying or via dropping the slurry into an oil bath, prior to being calcined. The monolith or microlith support may comprise or include materials such as, for example, silica, ceria, zirconia, titania, silicon carbide, a hydrotalcite material, such as MG30 (Sasol), tungsten carbide, aluminum nitride, alumina, mixed metal oxide ceramic or mixtures of two or more thereof.

Fluidizable Particles

It is contemplated that the microporous crystalline metallosilicates (e.g., zeolite) crystals, such as but not limited to those discussed above, could be formed into fluidizable particles. A fluidizable particle, for example, may be formed by deagglomerating the sodium form zeolite crystals (e.g., Na-ZSM-5), and then the crystals are contacted with sources of the desired Group 10 metal of the Periodic Chart, such as platinum, platinum and silver or platinum and copper, to form a metal-containing Na-ZSM-5. The metal-containing Na-ZSM-5 may be heat treated.

The metal-containing zeolite could be mixed with a binder, a matrix material. The binder could be a mixture of inorganic oxide materials, such as silica, alumina, titania, zirconia and clays such as kaolin and bentonite to form an aqueous slurry. The matrix could be peptized. Any surface acidity of alumina in the binder could be either minimized or controlled through the addition of alkaline metals, alkaline earth metals or a source of phosphorus to the spray dry slurry. The slurry may be dried, such as by spray drying and then calcined to form a fluid powder of, for example, less than 200 microns in diameter. Optionally, the acidity of the alumina could be controlled by post-treatment with sources of alkaline metals or alkaline earth metals such as by impregnation. Such materials are well known in the art of catalysts for fluidized bed processes such as ZSM-5 containing additive catalysts for the enhanced production of olefins in FCC (e.g., U.S. Pat. Nos. 5,456,821 and 5,888,378) and the production of pyridine and alkylpyridines (e.g., U.S. Pat. No. 5,994,550). The formulated catalyst composition could be calcined, and deployed in the process for producing cyclic $C_5$ compounds herein.

Passivation of Binder Alumina

It is contemplated that the detrimental role of the alumina in the catalytic performance of the formulated catalyst composition could be reduced by passivating the alumina. Passivation may be accomplished by either treating the formulated catalyst composition with at least one oxide modifier (with or without the addition of a source of phosphorus) and/or by an additional processing step, such as for example, by steaming.

The formulated catalyst composition which comprises alumina in Example 20, discussed below, may be treated with an oxide modifier or treated with a phosphorus containing compound. The microporous crystalline metallosilicate, such as a zeolite, may be contacted with a source of phosphorus prior to contacting with the binder components.

In one alternative, a source of phosphorus could be contacted with the aqueous slurry, and then the formulated catalyst composition may be heat treated to yield phosphorus oxide.

In another alternative, the formulated catalyst composition may be treated with an oxide modifier, such as for example, an additional source of silica either as a component in the aqueous slurry or as part of a treatment of the formulated catalyst composition.

It may be desirable to treat the formulated catalyst composition with more than one oxide modifier, including oxides of phosphorus and silicon, as well as oxides selected from the metals of Group 1 or Group 2 of the Periodic Chart.

Alternatively, a similar result could potentially be obtained through a catalyst processing step such as steaming the catalyst for a time and at a temperature which modifies the impact of the alumina on the catalytic performance.

The formulated catalyst composition of this invention is periodically rejuvenated and/or regenerated to remove coke from the composition which has accumulated during use of the composition and optionally oxychlorinated to redisperse metal.

Reactors

The process of this invention may be conducted in any suitable reactor. The contacting step of the process may be conducted in one of more reactors. Suitable reactors for the process include and may be selected from the group consisting of a fluidized bed, a moving bed, a fixed bed or a tubular reactor, radiantly heated tubular reactor, convectively heated tubular reactor, cyclical fixed bed reactor, circulating fluid bed reactor, radiantly heated fluid bed reactor, convectively heated fluid bed reactor, adiabatic reactor and/or electrically heated reactor.

Products and Articles

The process for producing cyclic $C_5$ compounds of this invention comprises one or more cyclic $C_5$ compositions. Such composition comprises one or more cyclic $C_5$ compounds. These cyclic $C_5$ compounds include and are selected from the group consisting of cyclopentadiene, dicyclopentadiene, cyclopentene, cyclopentane, pentene, pentadiene, and reaction products of two or more thereof.

The cyclic $C_5$ compounds may be reacted with a substrate to form a product. In some embodiments, the substrate comprise a double bond. Such product includes is one or more of a cyclopentadiene, cyclic olefin copolymers, cyclic olefin polymers, polycyclopentene, ethylidene norbornene, EPDM rubber, alcohols, plasticizers, blowing agents, solvents, octane enhancers, gasoline, unsaturated polyester resins, hydrocarbon resin tackifiers, formulated epoxy resins, polydicyclopentadiene, metathesis polymers of norbornene or substituted norbornenes or dicyclopentadiene, tetracyclodocene, or any combination of two or more thereof. The Diels Alder reaction derivatives of cyclopentadiene is or comprises norbornene or substituted norbornenes.

The product may be made into a useful article. Such article comprise any of the products made or derived from the process of this invention. Particularly, the article may be one or more of wind turbine blades, composites containing glass or carbon fibers, and formulated adhesives.

EXAMPLES

Measurement of Alpha Value

The Alpha Value tests for the materials or compositions in the Examples were performed in accordance with the methods described in U.S. Pat. No. 3,354,078 and in the Journal of Catalysis, Vol. 4, p. 527 (1965); Vol. 6, p. 278 (1966) and Vol. 61, p. 395 (1980), each incorporated herein by reference. The experimental conditions of the test included a constant temperature of 538° C. and a variable flow rate as described in detail in the Journal of Catalysis, Vol. 61, p. 395 (1980). When Group 10 or optional Group 11 metals were present, the Alpha value was measure prior to metal addition.

Measurement of Total Surface Area by BET

The total BET was measured by nitrogen adsorption/desorption with a Micromeritics Tristar II 3020 instrument after degassing of the calcined zeolite powders for 4 hrs at 350° C. More information regarding the method can be found, for example, in "Characterization of Porous Solids and Powders: Surface Area, Pore Size and Density", S. Lowell et al., Springer, 2004.

Example 1

Synthesis of ZSM-5 Crystals

A mixture with about 22% solids was prepared from 8,800 g of deionized (DI) water, 600 g of 50% NaOH solution, 26 g of 43% sodium aluminate solution, 730 g of n-propyl amine 100% solution, 40 g of ZSM-5 seed crystals, and 3,190 g of Ultrasil silica were mixed and then charged into an autoclave after mixing. The mixture had the following molar composition:

| | |
|---|---|
| $SiO_2/Al_2O_3$ | about 470 |
| $H_2O/SiO_2$ | about 12.1 |
| $OH/SiO_2$ | about 0.16 |
| $Na/SiO_2$ | about 0.16 |
| n-PA/Si | about 0.25. |

The mixture was mixed and reacted at 230° F. (110° C.) at 350 rpm for 48 hours. The resulting reaction slurry was discharged and stored in container. The X-ray diffraction (XRD) pattern (not shown) of the as-synthesized material showed the typical pure phase of ZSM-5 topology. The scanning electron microscope (SEM) image of the as-synthesized material shows that the material (not shown) was composed of mixture of crystals with size of about 1-2 micron. The resulting ZSM-5 crystals had a $SiO_2/Al_2O_3$ molar ratio of about 498, Na % of about 0.37 wt %, total surface area (SA)/(micropore SA+mesopore SA) of 468/(422+45) $m^2$/g.

Example 2

Preparation of Extrudate with Platinum Added Via Incipient Wetness Impregnation

A sample from Example 1 in the sodium form was used to prepare a 65 wt % ZSM-5 and 35 wt % silica extrudate. Sixty-five (65) parts by weight of zeolite were mulled with 35 parts by weight of silica. The silica was equally supplied by Ultrasil silica (obtainable from Evonik) and by Ludox HS-40 (obtainable from Sigma-Aldrich). Sufficient water was added to produce a mull mix of about 63 wt % solids. The material was extruded into 1/16" (1.59 mm) cylinders. After drying, was calcined for 6 hours in nitrogen at 900° F. (483° C.). After cooling, the sample was re-heated to 900° F. (483° C.) in nitrogen and held for three hours. The atmosphere was then gradually changed to 1.1%, 2.1%, 4.2%, and 8.4% oxygen in four stepwise increments. Each step was followed by a thirty minute hold. The temperature was increased to 1000° F. (538° C.), the oxygen content was increased to 16.8%, and the material was held at 1000° F. (538° C.) for 6 hours. After cooling, about 0.572 wt % Pt as measured by X-ray fluorescence (XRF) was added via incipient wetness impregnation using an aqueous solution of tetraamine platinum hydroxide. The catalyst was dried in air at room temperature then at 250° F. (121° C.), and calcined in air for three hours at 660° F. (349° C.).

Example 3

Preparation of Extrudate with Platinum Added Via the Muller

Another sample from Example 1 was used to prepare a 65 wt % Na-ZSM-5 and 35 wt % silica particle with platinum incorporated in the muller. 65 parts by weight of zeolite were mulled with sufficient tetraamine platinum hydroxide to result in about 0.31 wt % Pt on the finished catalyst as measured by XRF. This platinum source and zeolite were further mulled with 35 parts by weight of silica. The silica was equally supplied by Ultrasil silica and by Ludox HS-40. Sufficient water was added to produce a mull mix of 59 wt % solids. The material was extruded into 1/16" (1.59 mm) cylinders. After drying, was calcined for 6 hours in nitrogen at 900° F. (483° C.). After cooling, the sample was re-heated to 900° F. (483° C.) in nitrogen and held for three hours. The atmosphere was then gradually changed to 1.1%, 2.1%, 4.2%, and 8.4% oxygen in four stepwise increments. Each step was followed by a thirty minute hold. The temperature was increased to 1000° F. (538° C.), the oxygen content was increased to 16.8%, and the material was held at 1000° F. (538° C.) for 6 hours.

Example 4

On-Oil Testing of Examples 2 and 3

The extrudate samples of Example 2 and Example 3 were evaluated for performance. The catalyst (0.5 g crushed and sieved to 20-40 mesh) was physically mixed with quartz (1.5 g, 60-80 mesh) and loaded into a reactor. The catalyst bed was held in place with quartz wool and the reactor void space was loaded with coarse silicon carbide (SiC) particles. The reactor was loaded onto the unit and pressure tested to ensure no leaks. The catalysts were dried for 1 hour under helium (He) (100 mL/min, 30 psig, 250° C.) then reduced for 4 hours under hydrogen ($H_2$) (200 mL/min, 30 psig, 500° C.). The catalyst was then tested for performance with feed of n-pentane, $H_2$, and balance He, typically at 550° C.-600° C., 5.0 psia $C_5H_{12}$, 1.0 molar $H_2:C_5H_2$, 14.7 $h^{-1}$ WHSV, and 30 psig total. Catalyst stability and regenerability was tested post initial tests at 550-600° C. by stripping with $H_2$ (200 mL/min, 30 psig, 650° C.) for 5 hours then retesting performance at 600° C.

Figure 4A:
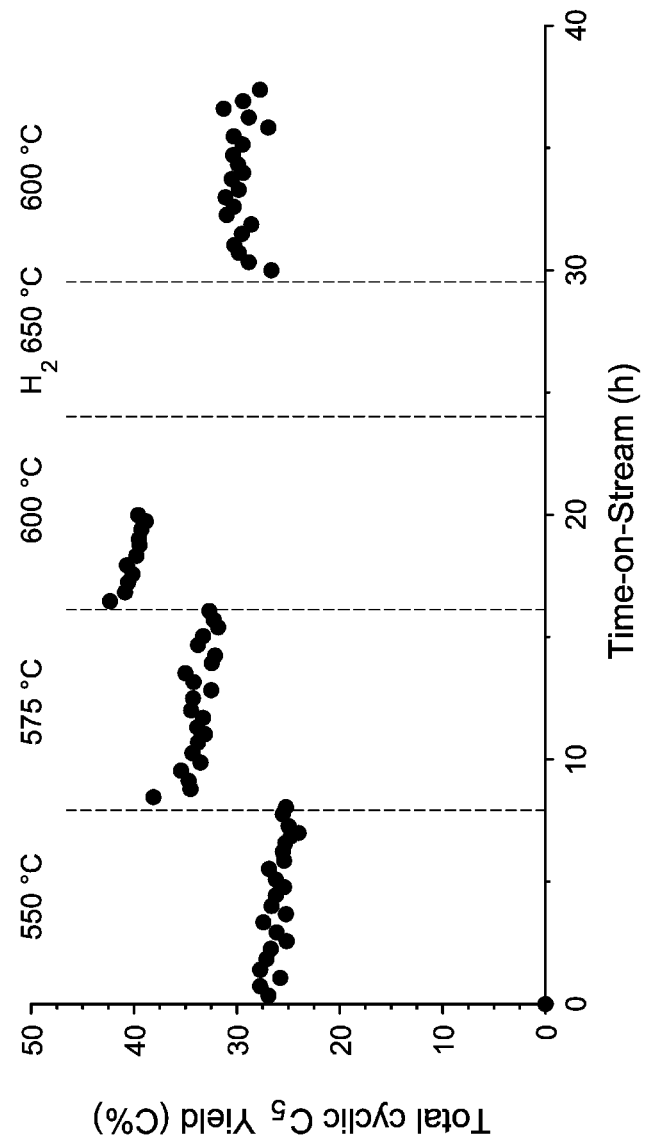
FIG. 4A shows the total yield to cyclic C$_5$ as a percentage for Example 2.

In Table 1, below, the conversion of n-pentane and the selectivity/yield of cyclic $C_5$'s, CPD, $C_1$, and $C_{2-4}$ cracking products at temperatures of 550° C. to 600° C. for Example 2 are shown. In the Tables, "Conv." is "Conversion." Reported are the average values over 8 hours at each temperature under conditions of: 0.5 g sample from Example 2, 5.0 psia $C_5H_{12}$, 1:1 molar $H_2:C_5$, 14.7 WHSV, 30 psig total. The total yield to cyclic $C_5$ as a percentage for Example 2 is shown in FIG. 4A.

TABLE 1

| | Conv. (%) | Selectivity (C %) | | | | | Yield (C %) | | | | | |
|---|---|---|---|---|---|---|---|---|---|---|---|---|
| Temp. (° C.) | $C_5H_{12}$ | $cC_5$ | CPD | $C_1$ | $C_{2-4}$ | $iC_5$ | $cC_5$ | CPD | $C_1$ | $C_{2-4}$ | $iC_5$ | $cC_5:C_{1-4}$ |
| 550 | 61 | 43 | 24 | 1.2 | 7.7 | 5 | 26 | 15 | 0.8 | 4.7 | 3 | 4.8 |
| 575 | 72 | 47 | 31 | 1.7 | 9.8 | 3.8 | 34 | 23 | 1.2 | 7.1 | 2.8 | 4.1 |
| 600 | 79 | 51 | 39 | 2.0 | 10.9 | 3.2 | 40 | 30 | 1.6 | 8.6 | 2.6 | 4.0 |
| 600, Post $H_2$ | 39 | 37 | 30 | 1.1 | 5.6 | 1.8 | 21 | 17 | 0.6 | 3.2 | 1.0 | 5.4 |

Figure 4B:
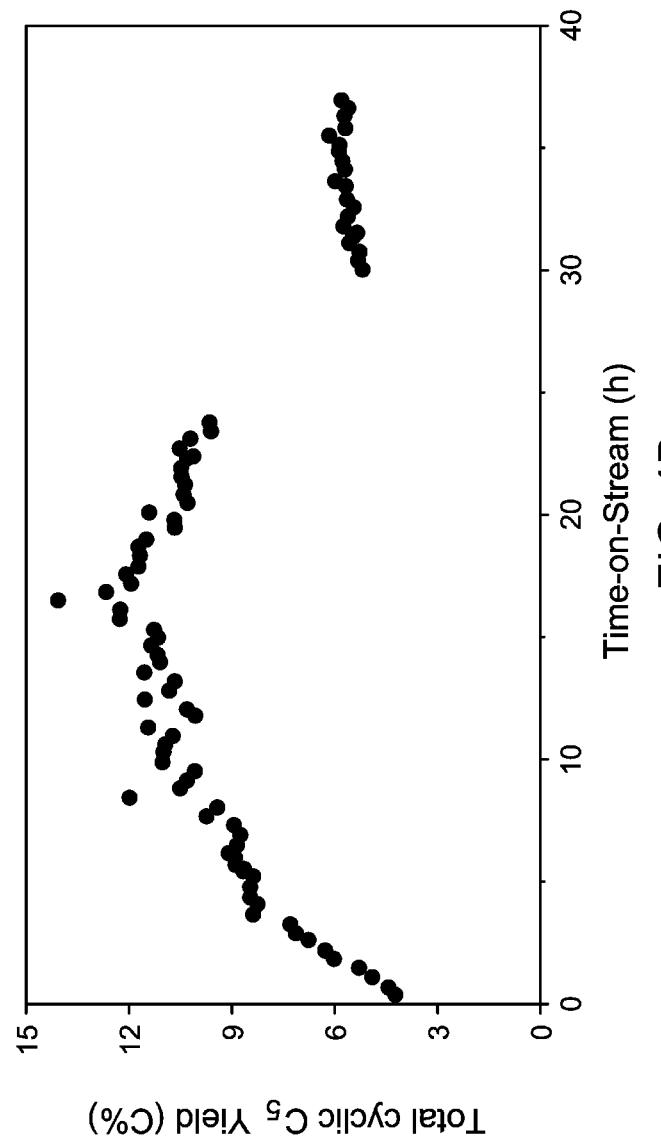
FIG. 4B shows the total yield to cyclic C$_5$ as a percentage for Example 3.

In Table 2, below, the conversion of n-pentane and selectivity/yield of cyclic $C_5$'s, CPD, $C_1$, and $C_{2-4}$ cracking products at temperatures in the range from 550° C. to 600° C. for Example 3 are shown. Reported are the average values over 8 hours at each temperature under conditions of 0.5 g sample of Example 3, 5.0 psia $C_5H_{12}$, 1:1 molar $H_2$:$C_5$, 14.7 WHSV, 30 psig total. The total yield to cyclic $C_5$ as a percentage for Example 3 is shown in FIG. 4B.

TABLE 2

| | Conv. (%) | Selectivity (C %) | | | | | Yield (C %) | | | | | |
| --- | --- | --- | --- | --- | --- | --- | --- | --- | --- | --- | --- | --- |
| Temp. (° C.) | $C_5H_{12}$ | $cC_5$ | CPD | $C_1$ | $C_{2-4}$ | $iC_5$ | $cC_5$ | CPD | $C_1$ | $C_{2-4}$ | $iC_5$ | $cC_5$:$C_{1-4}$ |
| 550 | 19 | 39 | 29 | 1.0 | 4.3 | 3 | 8 | 6 | 0.2 | 0.9 | 1 | 7.3 |
| 575 | 27 | 41 | 33 | 1.6 | 7.1 | 2.5 | 11 | 9 | 0.4 | 1.9 | 0.7 | 4.7 |
| 600 | 27 | 41 | 36 | 2.0 | 10.3 | 2.3 | 11 | 10 | 0.6 | 2.8 | 0.6 | 3.3 |
| 600, Post $H_2$ | 20 | 29 | 25 | 1.4 | 11.4 | 2.9 | 6 | 5 | 0.3 | 2.3 | 0.6 | 2.2 |

The methods of Pt addition to the zeolite-containing composition by adding Pt to the extrudate after extrusion by incipient wetness (Example 2) or adding Pt to the muller mixture, prior to extrusion (Example 3) were investigated. Both compositions were tested on-oil, with Example 2, exhibiting much greater activity (evidenced by n-pentane conversion). As seen in Table 2, there is a 60-70% conversion of n-pentane (an acyclic $C_5$) at 550° C.-600° C. for Pt added to the extrudate by incipient wetness of Example 2. This contrasts with a 20%-30% conversion for Pt added to the muller for Example 3. Selectivity to cyclic $C_5$ products was similar for the two compositions (40-50 C %), but the yield was much greater with Example 2 as compared to Example 3. The procedure for Pt addition to the zeolite support is crucial to ensure Pt intimacy with the zeolite, and not with the binder material.

Example 5

Synthesis of ZSM-5 Crystals Containing Silver

A mixture with about 22% solids was prepared from 9,400 g of DI water, 535 g of 50% NaOH solution, 768 g of n-propyl amine (n-Pa) 100% solution, 20 g of ZSM-5 seed crystals, 44 g of silver nitrate (>99%), and 3,360 g of Sipernat-340 silica were mixed in a container and then charged into an autoclave after mixing. The mixture had the following molar composition:

| | |
| --- | --- |
| $SiO_2$/$Al_2O_3$ | >800 |
| $H_2O$/$SiO_2$ | about 11 |
| $OH$/$SiO_2$ | about 0.17 |
| $Na$/$SiO_2$ | about 0.16 |
| n-PA/Si | about 0.25. |

The mixture was mixed and reacted at 230° F. (110° C.) at 250 rpm for 48 hours. The resulting reaction slurry was discharged and stored in a container. The XRD pattern (not shown) of the as-synthesized material showed the typical pure phase of ZSM-5 topology. The SEM of the as-synthesized material (not shown) exhibited that the material was composed of mixture of crystals with size of 1-2 micron. The as-synthesized zeolite crystals had a $SiO_2$/$Al_2O_3$ molar ratio of about 1043, Na of about 0.22 wt %, and Ag of about 0.95 wt %.

A sample of this zeolite crystal in the sodium form was calcined for 6 hours in nitrogen at 900° F. (483° C.). After cooling, the sample was re-heated to 900° F. (483° C.) in nitrogen and held for three hours. The atmosphere was then gradually changed to 1.1%, 2.1%, 4.2%, and 8.4% oxygen in four stepwise increments. Each step was followed by a thirty minute hold. The temperature was increased to 1000° F. (538° C.), the oxygen content was increased to 16.8%, and the sample was held at 1000° F. (538° C.) for 6 hours. After cooling, about 0.44 wt % Pt as measured by XRF was added via incipient wetness impregnation using an aqueous solution of tetraamine platinum hydroxide. The catalyst was dried in air at room temperature then at 250° F. (121° C.), and calcined in air for three hours at 660° F. (349° C.).

Example 6

Preparation of Extrudate with Pt Added Via Tetraamine Platinum Hydroxide Impregnation A sample of the zeolite crystals of Example 5 in the sodium form was used to prepare a 65 wt % zeolite and 35 wt % silica particle. Sixty-five parts by weight of zeolite were mulled with 35 parts by weight of silica. The silica was equally supplied by Ultrasil silica and by Ludox HS-40. Sufficient water was added to produce a mull mix of about 63 wt % solids. The material was extruded into 1/16" (1.59 mm) cylinders. After drying, was calcined for six hours in nitrogen at 900° F. (483° C.). After cooling, the sample was re-heated to 900° F. (483° C.) in nitrogen and held for three hours. The atmosphere was then gradually changed to 1.1%, 2.1%, 4.2%, and 8.4% oxygen in four stepwise increments. Each step was followed by a thirty minute hold. The temperature was increased to 1000° F. (538° C.), the oxygen content was increased to 16.8%, and the material was held at 1000° F. (538° C.) for six hours. After cooling, about 0.44 wt % Pt as measured by XRF was added a portion of the extrudate via incipient wetness impregnation using an aqueous solution of tetraamine platinum hydroxide. The catalyst was dried in air at room temperature then at 250° F. (121° C.), and calcined in air for three hours at 660° F. (349° C.). The catalyst was then sized to 20/40 mesh for catalytic evaluation.

Example 7

Preparation of Extrudate with Platinum Added Via Tetraamine Platinum Nitrate Impregnation Another portion of the calcined extrudate of Example 6 was sampled prior to the metal impregnation. about 0.48 wt % Pt as measured by XRF was added via incipient wetness impregnation using an aqueous solution of tetraamine platinum nitrate. The catalyst was dried in air at room temperature then at 250° F. (121° C.), and calcined in air for three hours at 660° F. (349° C.). The catalyst was then sized to 20/40 mesh for catalytic evaluation.

Example 8

On-Oil Testing of Examples 5 to 7

The catalyst sample of Example 5 was evaluated as follows. A sample of 0.2-0.8 grams was physically mixed with an appropriate amount of high-purity SiC (40-60 mesh) and loaded into a reactor. The amount of SiC was adjusted so that the overall length of the catalyst bed was 6 in. The catalyst bed was held in place with quartz wool and the reactor void space was loaded with coarse SiC particles. The reactor was loaded onto the unit and pressure tested to ensure no leaks. The catalyst samples were dried for 2 hours under helium (He) at 200 mL/min, 60 psia, 250° C., then reduced for 4 hour under $H_2$ (200 mL/min, 60 psia, 500° C.).

A feed consisting of 7.0 psia n-pentane, 7.0 psia $H_2$ and balancing He was introduced to the catalyst bed. The total pressure was 60 psia. The catalyst was de-edged at 550° C. for 8 hours at a WHSV of 3000 (g n-pentane/g Pt $h^{-1}$) and then tested at 575° C. for 24 hours at a WHSV of 6000 (g n-pentane/g Pt $h^{-1}$).

The average cyclopentadiene yield (C %) and selectivity, defined as the cyclo-$C_5$ yield (C %) divided by the sum of $C_1$-$C_4$ yields (C %), for Example 5 over the first 15 hours of testing were 19.5% and 4.6, respectively.

The extrudate samples (0.2-0.8 g) of Examples 6 and 7 were physically mixed with an appropriate amount of high-purity SiC (40-60 mesh) and loaded into a reactor. The amount of SiC was adjusted so that the overall length of the catalyst bed was 6 in. The catalyst bed was held in place with quartz wool and the reactor void space was loaded with coarse SiC particles. The reactor was loaded onto the unit and pressure tested to ensure no leaks. The catalyst was dried for 2 hour under He (100 mL/min, 60 psia, 250° C.) then reduced for 4 hour under $H_2$ (200 mL/min, 60 psia, 500° C.).

A feed consisting of 5.0 psia n-pentane, 5 psia $H_2$ and balancing He was introduced to the catalyst bed. The WHSV was 2928 (g pentane/g Pt $h^{-1}$) and the total pressure was 60 psia. The catalyst was de-edged at 550° C. for 8 hours and then tested at 575° C. for 24 hours.

The average cyclopentadiene yield (C %) and selectivity, defined as the cyclo-$C_5$ yield (C %) divided by the sum of $C_1$-$C_4$ yields (C %), for Example 6 over the first 15 hours of testing were 24.1% and 4.3, respectively.

The average cyclopentadiene yield (C %) and selectivity for Example 7 over the first 15 hours of testing were 22.4% and 3.8, respectively.

Example 9

Synthesis of ZSM-5 Crystals

A mixture with about 22% solids was prepared from 8,800 g of DI water, 600 g of 50% NaOH solution, 26 g of 43% sodium aluminate solution, 730 g of n-propyl amine 100% solution, 20 g of ZSM-5 seed crystals, and 3,190 g of Sipernat-340 silica were mixed in a container and then charged into an autoclave after mixing. The mixture had the following molar composition:

| | |
|---|---|
| $SiO_2/Al_2O_3$ | about 470 |
| $H_2O/SiO_2$ | about 10.7 |
| $OH/SiO_2$ | about 0.16 |
| $Na/SiO_2$ | about 0.16 |
| n-PA/Si | about 0.25. |

The mixture was mixed and reacted at 210° F. (99° C.) at 350 rpm for 72 hours. The resulting reaction slurry was discharged and stored in a container. The XRD pattern (not shown) of the as-synthesized material showed the typical pure phase of ZSM-5 topology. The SEM (not shown) of the as-synthesized material, shows that the material was composed of mixture of crystals with size of 0.5-1 micron. The as-synthesized crystals had a $SiO_2/Al_2O_3$ molar ratio of about 467 and Na of about 0.25 wt %.

Example 10

Preparation of Extrudate: ZSM-5 with Silica Binder

A sample of the zeolite of Example 9 in the sodium form was used to prepare a 65 wt % zeolite and 35 wt % silica composition. Sixty-five parts by weight of zeolite crystals were mulled with 35 parts by weight of silica. The silica was equally supplied by Ultrasil silica and by Ludox HS-40. Sufficient water was added to produce a mull mix of about 64 wt % solids. The material was extruded into 1/16" (1.59 mm) cylinders. After drying, was calcined for 6 hours in nitrogen at 900° F. (483° C.). After cooling, the sample was re-heated to 900° F. (483° C.) in nitrogen and held for three hours. The atmosphere was then gradually changed to 1.1%, 2.1%, 4.2%, and 8.4% oxygen in four stepwise increments. Each step was followed by a thirty minute hold. The temperature was increased to 1000° F., the oxygen content was increased to 16.8%, and the material was held at 1000° F. for 6 hours.

Example 11

Preparation of Silicone Treated Extrudate

A portion of the extrudate of Example 10 was impregnated with a solution containing about 7.8 parts Dow 550 Silicone per 100 parts of extrudate in decane. The impregnated sample was dried. It was then calcined by heating in nitrogen at 30 degrees F./minute to 1000° F. (538° C.) and held at 1000° F. (538° C.) for one hour. The catalyst was cooled to 950° F. (510° C.). Air was added to 40 vol % air/60 vol % nitrogen and the temperature was raised to 1000° F. (538° C.) and held for 6 hours. After cooling, about 0.46 wt % Pt as measured by XRF was added via incipient wetness impregnation using an aqueous solution of tetraamine platinum nitrate. The catalyst was dried in air at room temperature then at 250° F. (121° C.), and calcined in air for three hours at 660° F. (349° C.). The catalyst was then sized to 20/40 mesh for catalytic evaluation.

Example 12

On-Oil Testing of Example 11

An extrudate sample (0.2-0.8 g) of Example 11 was physically mixed with an appropriate amount of high-purity SiC (40-60 mesh) and loaded into a reactor. The amount of SiC was adjusted so that the overall length of the catalyst bed was 6 in. The catalyst bed was held in place with quartz wool and the reactor void space was loaded with coarse SiC particles. The reactor was loaded onto the unit and pressure tested to ensure no leaks. The catalyst was dried for 2 hour under He (200 mL/min, 60 psia, 250° C.) then reduced for 4 hour under $H_2$ (200 mL/min, 60 psia, 500° C.).

A feed consisting of 5.0 psia 1-pentene, 10.0 psia $H_2$ and balancing He was introduced to the catalyst bed. The total pressure was 60 psia. The catalyst was de-edged at 550° C. for 8 hours at a WHSV of 3000 (g 1-pentene/g Pt h$^{-1}$) and then tested at 575° C. for 24 hours at a WHSV of 6000 (g 1-pentene/g Pt h$^{-1}$).

The average cyclopentadiene yield (C %) and selectivity, defined as the cyclo-C$_5$ yield (C %) divided by the sum of C$_1$-C$_4$ yields (C %), for Example 10 over the first 15 hours of testing are 18.6 and 2.2, respectively.

Example 13

Preparation of Extrudate with Target 3:1 Molar Ratio of Copper to Platinum

The zeolite crystals of Example 9 in the sodium form was used to prepare a 65 wt % zeolite and 35 wt % silica particle. 65 parts by weight of zeolite were mulled with 35 parts by weight of silica. The silica was equally supplied by Ultrasil silica and by Ludox HS-40. Sufficient water was added to produce a mull mixture of about 62.5 wt % solids. The mull mixture was extruded into ⅟₁₆" (1.59 mm) cylinders extrudates. After drying, the extrudates were heated to 900° F. (483° C.) in nitrogen and held for three hours. The atmosphere was then gradually changed to 1.1, 2.1, 4.2, and 8.4% oxygen in four stepwise increments. Each step was followed by a thirty minute hold. The temperature was increased 1000° F. (538° C.), the oxygen content was increased to 16.8%, and the material was held at 1000° F. (538° C.) for 6 hours and cooled.

A portion of the calcined extrudate was then impregnated sequentially via incipient wetness impregnation. First, the calcined extrudate sample was impregnated with copper (II) nitrate hydrate and dried for 4 hours at 250° F. (121° C.). Second, the calcined extrudate sample was impregnated with tetraamine platinum nitrate and dried. The impregnated extrudate was then calcined for three hours in air at 660° F. (349° C.). Sufficient platinum was added to target about 0.325 wt % platinum on the extrudate to form a catalyst and sufficient copper was added to target a about 3:1 molar copper: platinum ratio.

Example 14

Synthesis of ZSM-5 with Target 3:1 Molar Ratio of Copper to Platinum

A second batch of the same calcined extrudate as described in Example 13, above, was prepared. A 20 gram portion of the calcined extrudate was impregnated with copper (II) nitrate hydrate and dried for 4 hours at 250° F. (121° C.). It was then impregnated with tetraamine platinum nitrate and dried. The impregnated extrudate was dried at 250° F. (121° C.), and then calcined for three hours in air at 660° F. (349° C.) to form a catalyst that contained about 0.31 wt % Cu and about 0.32 wt % Pt by XRF.

Example 15

On-Oil Testing of Examples 13 and 14

The catalyst samples (0.2-0.8 g) of Examples 13 and 14 were physically mixed with an appropriate amount of high-purity SiC (40-60 mesh) and loaded into a reactor. The amount of SiC was adjusted so that the overall length of the catalyst bed was 6 in. The catalyst bed was held in place with quartz wool and the reactor void space was loaded with coarse SiC particles. The reactor was loaded onto the unit and pressure tested to ensure no leaks. Each catalyst sample was dried for 2 hour under He (200 mL/min, 60 psia, 250° C.) then reduced for 4 hour under H$_2$ (200 mL/min, 60 psia, 500° C.).

A feed consisting of 5.0 psia 1-pentene, 10.0 psia H$_2$ and balancing He was introduced to the catalyst bed. The total pressure was 60 psia. The catalyst was de-edged at 550° C. for 8 hours at a WHSV of 3000 (g 1-pentene/g Pt h$^{-1}$) and then tested at 575° C. for 24 hours at a WHSV of 6000 (g 1-pentene/g Pt h$^{-1}$).

The average cyclopentadiene yield (C %) and selectivity for Example 13 over the first 15 hours of testing are 10.8% and 3.7%, respectively.

The average cyclopentadiene yield (C %) and selectivity for Example 14 over the first 15 hours of testing are 13.7% and 4.2%, respectively.

Example 16

Synthesis of ZSM-5 with Target 6:1 Molar Ratio of Copper to Platinum

The zeolite of Example 9 in the sodium form was calcined for 6 hours in nitrogen at 900° F. (483° C.). After cooling, the sample was re-heated to 900° F. (483° C.) in nitrogen and held for three hours. The atmosphere was then gradually changed to 1.1%, 2.1%, 4.2%, and 8.4% oxygen in four stepwise increments. Each step was followed by a thirty minute hold. The temperature was increased to 1000° F. (538° C.), the oxygen content was increased to 16.8%, and the material was held at 1000° F. (538° C.) for 6 hours. A portion of the sample was impregnated with copper (II) nitrate hydrate and dried for 4 hours at 250° F. (121° C.). It was then impregnated with tetraamine platinum hydroxide and dried. The impregnated extrudate was dried at 250° F. (121° C.) then calcined for 1 hour in air at 610° F. (321° C.). The catalyst contained about 0.89 wt % Cu and about 0.58 wt % Pt by XRF.

Example 17

Synthesis of an Extruded ZSM-5 with Target 6:1 Molar Ratio of Copper to Platinum A portion of the same extruded and calcined extrudate as described in Example 14 was impregnated with copper (II) nitrate hydrate and dried for 4 hours at 250° F. (121° C.). It was then impregnated with tetraamine platinum nitrate and dried. The impregnated extrudate was dried at 250° F. (121° C.), then calcined for three hours in air at 660° F. (349° C.). The catalyst contained about 0.62 wt % Cu and about 0.33 wt % Pt by XRF.

Example 18

On-Oil Testing of Examples 16 and 17

The catalyst samples (0.2-0.8 g) of Examples 16 and 17 were each physically mixed with an appropriate amount of high-purity SiC (40-60 mesh) and loaded into a reactor. The amount of SiC was adjusted so that the overall length of the catalyst bed was 6 in. The catalyst bed was held in place with quartz wool and the reactor void space was loaded with coarse SiC particles. The reactor was loaded onto the unit and pressure tested to ensure no leaks. The catalyst samples were dried for 2 hours under He (200 mL/min, 60 psia, 250° C.) then reduced for 4 hour under $H_2$ (200 mL/min, 60 psia, 500° C.).

A feed consisting of 5.0 psia 1-pentene, 10.0 psia $H_2$ and balancing He was introduced to the catalyst bed. The total pressure was 60 psia. The catalyst was de-edged at 550° C. for 8 hours at a WHSV of 3000 (g 1-pentene/g Pt $h^{-1}$) and then tested at 575° C. for 24 hours at a WHSV of 6000 (g 1-pentene/g Pt $h^{-1}$).

The average cyclopentadiene yield (C %) and selectivity for Example 14 over the first 15 hours of testing are 19.0% and 3.3%, respectively.

The average cyclopentadiene yield (C %) and selectivity for Example 15 over the first 15 hours of testing are 14.8% and 4.5%, respectively.

Example 19

Synthesis of ZSM-5 of about 450:1 SiO2/Al2O3 Molar Ratio and about 0.3 Micron Crystal Size A mixture with about 22 wt % solids was prepared from 8,800 g of DI water, 600 g of 50% NaOH solution, 26 g of 43% sodium aluminate solution, 730 g of n-propyl amine 100% solution, 20 g of ZSM-5 (Si/$Al_2$ about 50/1) seed crystals, and 3,190 g of Sipernat-340 silica were mixed in a 5-gal pail container and then charged into a 5-gal autoclave after mixing. The mixture had the following molar composition:

| | |
|---|---|
| $SiO_2/Al_2O_3$ | about 470 |
| $H_2O/SiO_2$ | about 10.7 |
| $OH/SiO_2$ | about 0.16 |
| $Na/SiO_2$ | about 0.16 |
| n-PA/Si | about 0.25. |

The mixture was mixed and reacted at 210° F. (99° C.) at 350 rpm for 48 hours. The resulting reaction slurry was discharged and stored in a container. The XRD pattern (not shown) of the as-synthesized material showed the typical pure phase of ZSM-5 topology. The SEMs (not shown) of the as-synthesized material shows that the material was composed of mixture of crystals with uniform crystal size of about 0.3 micron. The as-synthesized Na-ZSM-5 crystals had a $SiO_2/Al_2O_3$ molar ratio of about 450 and Na of about 0.18 wt %.

Example 20

Preparation of Catalyst Slurry: ZSM-5/Kaolin Clay Silica and Alumina Binders

This example describes the preparation of a fluid catalyst slurry suitable for spray drying into fluidizable catalyst particles. A portion of the as-synthesized Na-ZSM-5 zeolite crystals of Example 19 was calcined and then impregnated sequentially with both 0.46 wt % copper via copper nitrate and 0.50 wt % platinum via tetraamine platinum nitrate. The metal-modified zeolite crystals were then calcined at 660° F. (349° C.) for three hours, and then incorporated into a slurry. An aqueous fluid catalyst slurry was prepared by mixing 40 wt % of this Na-ZSM-5, 30 wt % of a kaolin clay, and 30 wt % of a binder composed of 5 parts by weight silica (Ludox LS, obtainable from Sigma-Aldrich) and 1 part by weight formic acid peptized alumina (Condea Pural SBIII, obtainable from Sasol). The slurry was dried. After drying, the catalyst sample was calcined in air at 900° F. (349° C.) for three hours.

Example 21

On-Oil Testing of Example 20

The catalyst sample of Example 20 was evaluated as follows. A sample of 0.2-0.8 grams was physically mixed with an appropriate amount of high-purity SiC (40-60 mesh) and loaded into a reactor. The amount of SiC was adjusted so that the overall length of the catalyst bed was 6 in. The catalyst bed was held in place with quartz wool and the reactor void space was loaded with coarse SiC particles. The reactor was loaded onto the unit and pressure tested to ensure no leaks. The catalyst samples were dried for 2 hours under helium (He) (200 mL/min, 60 psia, 250° C.) then reduced for 4 hour under $H_2$ (200 mL/min, 60 psia, 500° C.).

A feed consisting of 7.0 psia n-pentane, 7.0 psia $H_2$ and balancing He was introduced to the catalyst bed. The total pressure was 60 psia. The catalyst was de-edged at 550° C. for 8 hours at a WHSV of 3000 (g n-pentane/g Pt $h^{-1}$) and then tested at 575° C. for 24 hours at a WHSV of 6000 (g n-pentane/g Pt $h^{-1}$).

The cyclopentadiene yield (C %), iso $C_5$ yield (C %) and selectivity, defined as the cyclo-$C_5$ yield (C %) divided by the sum of $C_1$-$C_4$ yields (C %), for Example 21 at t=10 h are 2.2%, 17.8% and 2.9, respectively, thus showing poor performance.

Example 22

Preparation of Catalyst Slurry: ZSM-5 and Si Binder

This example describes the preparation of a wash coat slurry suitable for wash coating onto monoliths, microliths, or other materials. Another portion of the as-synthesized Na-ZSM-5 zeolite crystals of Example 19 was calcined and then impregnated sequentially with both 0.46 wt % copper via copper nitrate and 0.50 wt % platinum via tetraamine platinum nitrate. The metal-modified zeolite crystals were then calcined at 660° F. (349° C.) for three hours, and then incorporated into a slurry. An aqueous fluid slurry was prepared by mixing 60 wt % of the Na-ZSM-5 of Example 19 and 40 wt % silica using a mixture of both a colloidal silica (30 wt %, obtainable from Alfa Aesar) and a fumed silica (10 wt %, Aerosil 200 obtainable from Evonik Industries). The slurry was dried. After drying, the catalyst sample was calcined in air at 900° F. (349° C.) for three hours.

Example 23

On-Oil Testing of Example 22

The catalyst sample of Example 22 was evaluated as follows. A sample of 0.2-0.8 grams was physically mixed with an appropriate amount of high-purity SiC (40-60 mesh) and loaded into a reactor. The amount of SiC was adjusted so that the overall length of the catalyst bed was 6 in. The catalyst bed was held in place with quartz wool and the reactor void space was loaded with coarse SiC particles. The reactor was loaded onto the unit and pressure tested to ensure no leaks. The catalyst samples were dried for 2 hours under helium (He) (200 mL/min, 60 psia, 250° C.) then reduced for 4 hour under $H_2$ (200 mL/min, 60 psia, 500° C.).

A feed consisting of 7.0 psia n-pentane, 7.0 psia $H_2$ and balancing helium (He) was introduced to the catalyst bed. The total pressure was 60 psia. The catalyst was de-edged at 550° C. for 8 hours at a WHSV of 3000 (g n-pentane/g Pt $h^{-1}$) and then tested at 575° C. for 24 hours at a WHSV of 6000 (g n-pentane/g Pt $h^{-1}$).

The cyclopentadiene yield (C %) and selectivity, defined as the cyclo-05 yield (C %) divided by the sum of $C_1$-$C_4$ yields (C %), for this Example 23 over the first 15 hours of testing are 13.0% and 8.9%, respectively.

In any embodiment and features have been described using a set of numerical upper limits and a set of numerical lower limits. It should be appreciated that ranges from any lower limit to any upper limit are contemplated unless otherwise indicated. Certain lower limits, upper limits, and ranges appear in one or more claims below. All numerical values take into account experimental error and variations that would be expected by a person having ordinary skill in the art.

All documents described herein are incorporated by reference herein, including any priority documents and/or testing procedures to the extent they are not inconsistent with this text. As is apparent from the foregoing general description and the specific embodiments, while forms of the invention have been illustrated and described, various modifications can be made without departing from the spirit and scope of the invention. Accordingly, it is not intended that the invention be limited thereby.

The invention claimed is:

1. A process for producing cyclopentadiene, the process comprising a step of contacting an acyclic $C_5$ feedstock with a formulated catalyst composition under acyclic $C_5$ conversion conditions effective to convert at least part of the acyclic $C_5$ feedstock to produce an effluent comprising cyclopentadiene, wherein the acyclic $C_5$ feedstock comprises acyclic $C_5$ hydrocarbons and optionally hydrogen, a light hydrocarbon or a mixture thereof, and the formulated catalyst composition consists of:
    (i) a microporous crystalline metallosilicate;
    (ii) a metal of Group 10 of the Periodic Table or a compound thereof, and optionally, a metal selected from the group consisting of rare earth metals, metals of Groups 8, 9, or 11 of the Periodic Table, mixtures or combinations thereof, or a compound thereof, and
    (iii) a binder selected from the group consisting of one or more of silica, titania, zirconia, metal silicates of Group 1, Group 2, or Group 13 of the Periodic Table or mixtures thereof,
    and additionally
    (iv) an alkali metal of Group 1 of the Periodic Table, or a compound thereof; and/or
    (v) an alkaline earth metal of Group 2 of the Periodic Table or a compound thereof, wherein the formulated catalyst composition is made into one or more of an extrudate, a spray dried particle, an oil drop particle, or a spherical particle, followed by impregnating the extrudate and/or particle with the Group 10 metal, and/or the optional Groups 8, 9, or 11 metals.

2. The process of claim 1, wherein the extrudate is a shaped extrudate.

3. The process of claim 2, wherein the shaped extrudate has a cylindrical form or a lobed form.

4. The process of claim 3, wherein the shaped extrudate having the lobed form is a symmetrical lobed form, an asymmetrical lobed form, a symmetrical spiral lobed form or an asymmetrical spiral lobed form.

5. The process of claim 1, wherein the microporous crystalline metallosilicate has a framework type selected from the group consisting of MWW, MFI, LTL, MOR, BEA, TON, MTW, MTT, FER, MRE, MFS, MEL, DDR, EUO, and FAU.

6. The process of claim 1, wherein the microporous crystalline metallosilicate is a microporous crystalline aluminosilicate.

7. The process of claim 6, wherein the microporous crystalline aluminosilicate is selected from the group consisting of zeolite beta, mordenite, faujasite, Zeolite L, ZSM-5, ZSM-11, ZSM-22, ZSM-23, ZSM-35, ZSM-48, ZSM-50, ZSM-57, ZSM-58, MCM-22 family material, and mixtures of two or more thereof.

8. The process of claim 1, wherein the binder is selected from the group consisting of one or more of silica, titania, zirconia, calcium silicate, magnesium silicate, or mixtures thereof.

9. The process of claim 8, wherein the binder contains less than 35 wt % clay and alumina.

10. The process of claim 1, wherein the alkali metal is selected from the group consisting of lithium, sodium, potassium, rubidium, cesium, and mixtures of two or more thereof.

11. The process of claim 1, wherein the alkaline earth metal is selected from the group consisting of beryllium, magnesium, calcium, strontium, barium, and mixtures of two or more thereof.

12. The process of claim 1, wherein the metallosilicate comprises aluminum and a molar ratio of the alkali metal to aluminum is at least 1 or a molar ratio of the alkaline earth metal to aluminum is at least 1.

13. The process of claim 1, wherein the metal of Group 10 is platinum.

14. The process of claim 1, wherein the optional metal is a Group 11 metal selected from copper or silver.

15. The process of claim 1, wherein the contacting occurs in one or more reactors selected from the group consisting of a fluidized bed, a moving bed, a fixed bed or a tubular reactor.

16. The process of claim 1, wherein the formulated catalyst composition is periodically rejuvenated and/or regenerated.

17. The process of claim 1, wherein the acyclic $C_5$ conversion conditions include at least a temperature of 450° C. to 650° C., a molar ratio of the optional hydrogen co-feed to the acyclic $C_5$ feedstock is in a range of 0.01 to 3, a molar ratio of the optional light hydrocarbon co-feed to the acyclic $C_5$ feedstock is in a range of 0.01 to 5, the acyclic $C_5$ feedstock has a partial pressure in a range of 3 psia to 100 psia at a reactor inlet (21 to 689 kPa-a), and the acyclic $C_5$ feedstock has a weight hourly space velocity in a range from 1 $hr^{-1}$ to 50 $hr^{-1}$.

* * * * *